United States Patent [19]

Morel et al.

[11] Patent Number: Plant 7,579

[45] Date of Patent: Jul. 2, 1991

[54] DIEFFENBACHIA CV. MORLEM

[75] Inventors: Vincent Morel, Antibes; Michel Morel, Golfe-Juan; Rene Riou, Antibes, all of France

[73] Assignee: Morel Freres S.N.C., Antibes, France

[21] Appl. No.: 360,250

[22] Filed: Jun. 1, 1989

[30] Foreign Application Priority Data

Jun. 13, 1988 [FR] France ..... 7791

[51] Int. Cl.[5] ..... A01H 5/00

[52] U.S. Cl. ..... Plt./88

[58] Field of Search ..... Plt./88, 89

[56] References Cited

U.S. PATENT DOCUMENTS

P.P. 2,869 2/1969 Chaplin ..... Plt. 88

*Primary Examiner*—James R. Feyrer

*Attorney, Agent, or Firm*—William H. Elliott, Jr.

[57] ABSTRACT

The invention concerns a new and distinct variety of Dieffenbachia cv. Morlem, originating as a sport of Dieffenbachia cv. Yellow Tropic and differing therefrom by its distinctive variegation that shows an extension of the yellow macule or coloration to substantially the whole leaf blade, excluding the central main vein, and deliniated by a distinctive green colored edge that extends around the entire circumference of the leaf without significant indentations toward the middle of the limb; this pattern of variegation and the combination of the colored areas give the new variety a luminous look which is typical of the Morlem variety; otherwise the Morlem variety has the characteristics of the parental Yellow Tropic variety.

3 Drawing Sheets

1

The present invention relates to a distinct and new variety of Dieffenbachia cv. Morlem. The plant belongs to the Amoena sub-species or group of Dieffenbachia Schott.; a plant of the family Araceae. The new plant originated as a sport of an unpatented Dieffenbachia cv. Yellow Tropic.

The Morlem sport was discovered by Vincent Morel growing on an axillary stem of a Yellow Tropic Dieffenbachia that was being grown in a cultivated state in a greenhouse of Morel Freres S.N.C. in Antibes, France. He was particularly attracted by the unusual and distinctive variegation and leaf coloring of the sport which appears as a large, generally regular, yellow blotch or macule covering substantially the entire central surface of the leaf, except for the main vein, and a rather well defined green colored edge that extends around the entire circumference of the leaf.

A cutting of the sport was rooted under the direction of Vincent Morel, and with the collaboration of Michel Morel and Rene Riou, the sport was vegetatively propagated to establish a collection of Morlem cultivar plants. Subsequent vegetative propagations of the Morlem cultivar over several generations have shown the mutation to be stable in its essential characteristics.

All the testing and evaluation of the cultivar led to the conclusion that Morlem represented a new and distinct variety which differed from the parent variety, as well as from all other known and referenced Dieffenbachia varieties, by the following combination of characteristics:

1. A general similarity to the Dieffenbachia Amoena group.
2. The same more compact and balanced plant habit and the same general sizes and shaped for the different organs (stems, petioles and leaves) as the parent variety, Yellow Tropic.
3. An unusual and distinctive variegation which appears on leaves with a large light yellow-green macule covering over 70% of the central area of the blade — except for the dark-green main vein — and surrounded

2 concentrically by a generally regular edge — also dark-green — that extends all around the circumference of the leaf without significant indentation from the edge to the heart of the blade as usually occurs in other known Amoena sports.

The Morlem type of variegation gives a visual impression close to the color distribution of another Dieffenbachia cultivar named Camilla that is linked to the Compacta group because of its small leaves and low plants.

Further, in the case of Morlem, and unlike Camillia and Amoena types, the central macule is not white or ivory, but lightly yellow green indicating the presence of active chlorophyll pigmentation in this part of the leaves, and, apparently because of the presence of the chlorophyll there is no lack in vigor for the variety in comparison with the parent variety.

Throughout the specification, color names beginning with a small letter signify that the name of the color as used in common speech is aptly descriptive; color names beginning with a capital letter designate color values based on the R.H.S. Colour Chart published by The Royal Horticultural Society of London, England.

To enable the identification of the MORLEM variety of Dieffenbachia, and compare it with its parent reference is made to the accompanying drawings (Sheets 1, 2, and 3) consisting of colored photographs of plants grown in our greenhouses in Antibes, France, and which show the distinctive characteristic features of the Morlem plant described herein.

Figure 2:
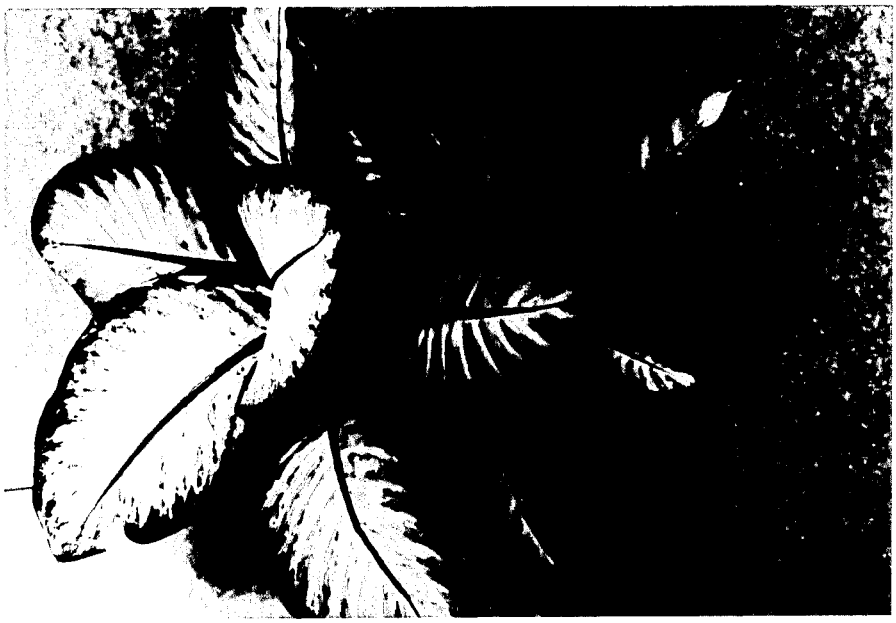
FIG. 2 shows a tall, mature plant of the new Morlem variety.
Figure 1:
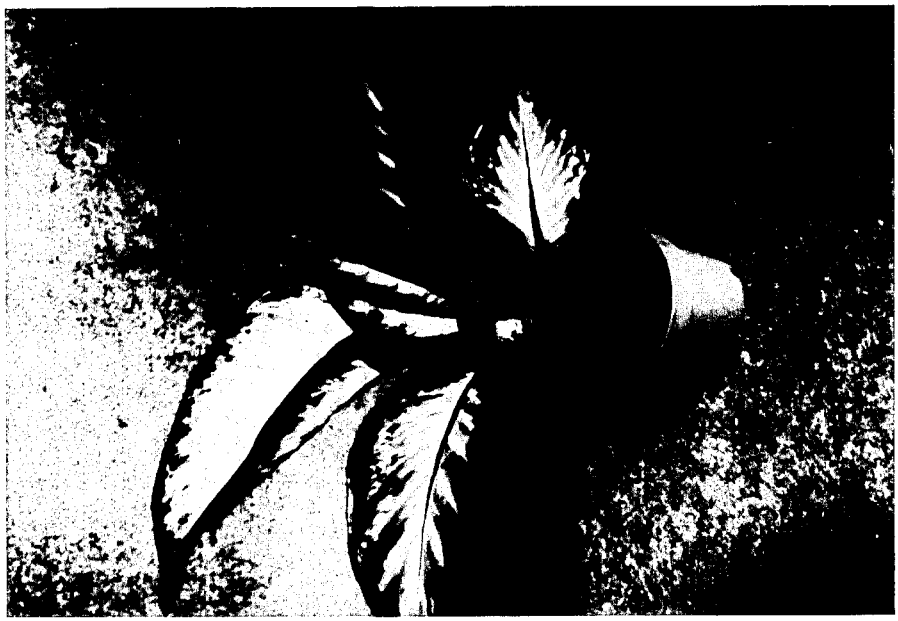
FIG. 1 shows a rooted cutting taken from the mother plant of the new Morlem variety.
Figure 3:
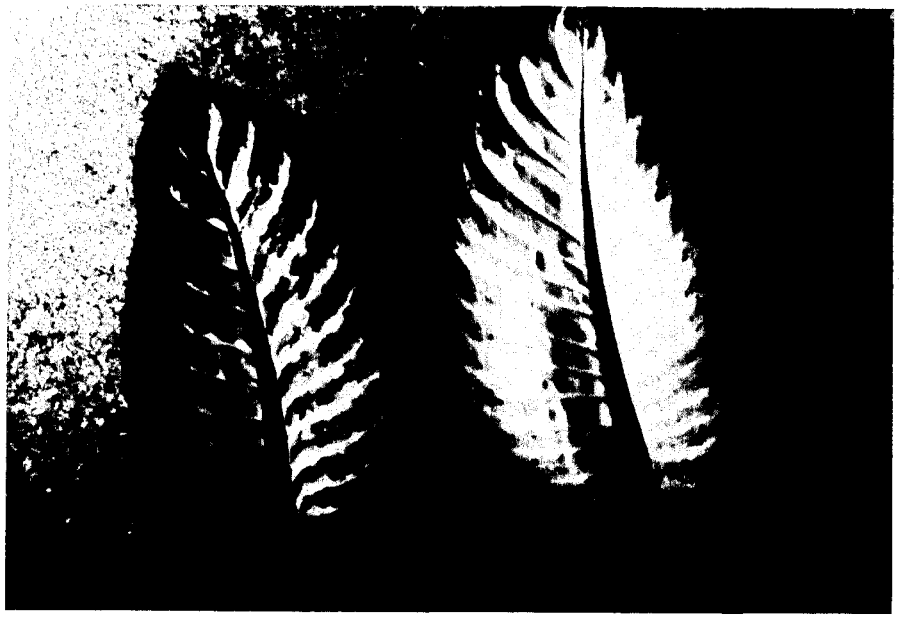
FIG. 3 shows the inside faces of the leaves of the parental Yellow Tropic variety (on the left) and of the new Morlem variety (on the right).
Figure 4:
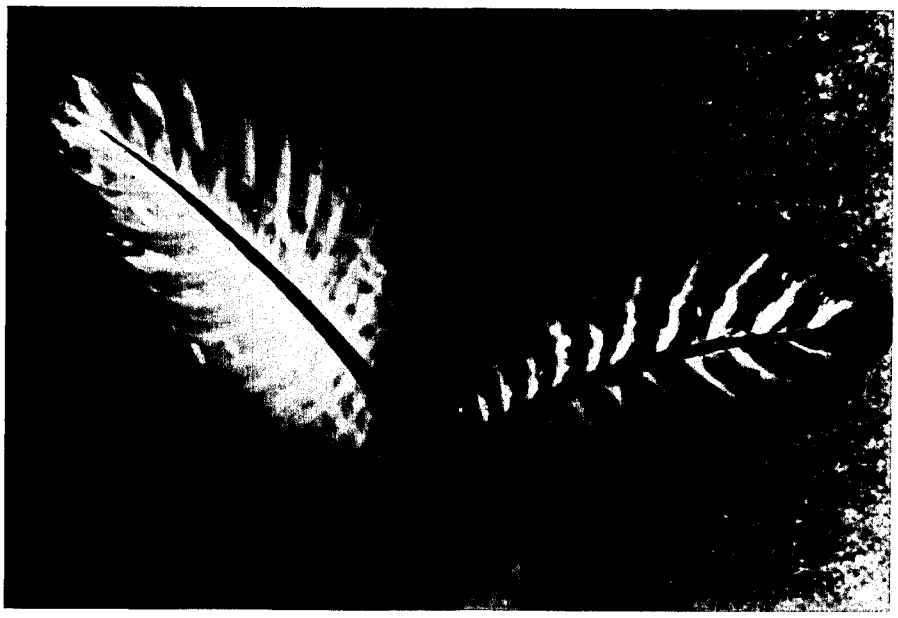
FIG. 4 shows the upper faces of leaves in the parental Yellow Tropic variety (on the right) and the new Morlem variety (on the left).
Figure 5:
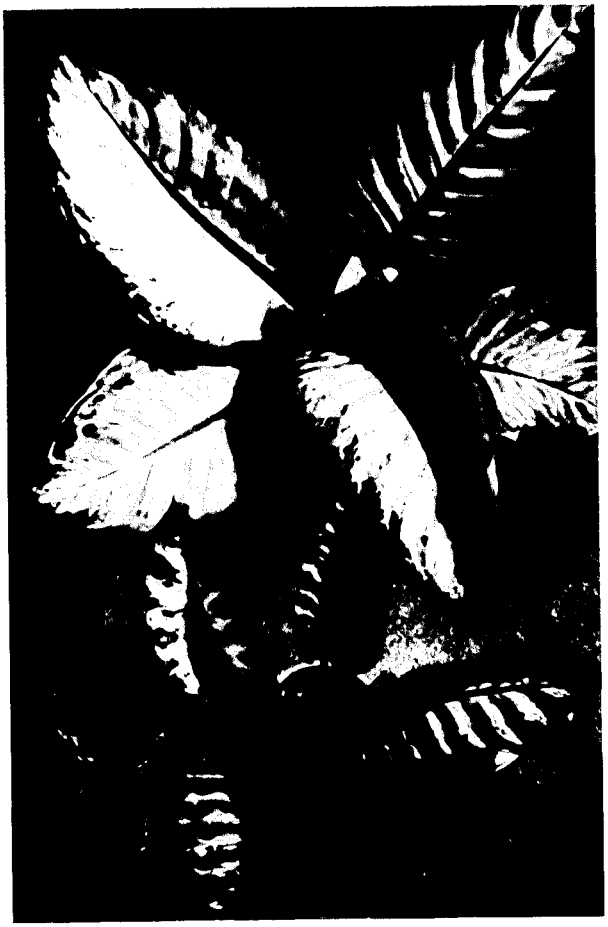
FIG. 5 shows the difference in coloring of the two adult plants; one is the new Morlem variety (in the upper portion of the photograph) and the other is the parental Yellow Tropic (in the lower portion of the photograph).

As can be seen in FIGS. 1-5, Morlem is clearly distinguishable from Yellow Tropic by its variegation that shows an extension of the yellow-green macule or coloration on over 70% of the whole leaf blade, excluding the central main vein. The macule is delimited by a very distinct homogenous green colored edge on the leaf that extends around the entire circumference of the leaf without appreciable indentation toward the middle part of the leaf. This type of variegation and the combination of the colored areas give to this new plant a luminous look which is typical of the Morlem variety. The buds and flowers of the Morlem are similar to those of Yellow Tropic.

The following botanical and descriptive characteristics of the Morlem Dieffenbachia listed below were made in accordance with test guidelines developed by the International Union for the Protection of New Varieties of Plants TWO/XX/19, dated Mar. 26, 1987, and are of plants asexually reproduced by applicants in the greenhouse of Morel Freres S.N.C. in Antibes, France.

DESCRIPTION

Characteristics: Morlem Variety

Plant:

*Growth habit.*—Slender — a bit more compact than most Amoena types.

*Height.*—Tall — between the 3 and 3½ months after rooting of cuttings, the plant is about 70 cm (26½") tall; generally like Amoena.

*Capacity for suckering.*—Weak to medium — little bit greater than most Amoena types, more like Carina or Veerle but close to Yellow Tropic.

*Blooming habit.*—Has never bloomed under conditions prevalent in our growing of the variety.

*Foliage.*—Normal for type.

*Stability of color distribution during aging of leaf.*—Rather stable — when plant is cut back, dark green spots appear in the central macule. Typical variegation is restored on aging of the plant. Similar to Amoena and Tropic White.

Main stem:

*Internodes.*—About 2 cm (¾") spacing on 70 cm (27½") plants.

*Diameter.*—Large — about 2.8 to 8 cm (1.1" to 2.4") on 60 cm (24") plants — like Amoena.

*Number of colors.*—One — like Amoena.

*Dominant color.*—Medium green — lighter than Amoena types.

*Secondary color.*—Not clearly distinct.

Petiole:

*Length in relation to that of blade.*—Short — about 1/7 of the blade length — like D. Pittieri.

*Number of colors.*—Two — like Yellow Tropic; Morlem is slightly lighter on inside surface — see FIGS. 3 and 4; upper surface about Green 139A; inside surface about Green 139B.

*Dominant color.*—Dark green.

Leaf:

*Texture.*—Smooth — on upper and under faces.

*Size.*—Large — about 35 cm (13¾") — like Amoena and Tropic White.

*Shape.*—Ovate with cordate base; like Amoena types.

*Width.*—Medium — about 18 to 20 cm (about 7"-7¾") in mature stage.

*Shape of apex.*—Medium acuminate — like Amoena types.

*Number of colors on upper side of main vein.*—One.

Leaf blade:

*Color distribution.*—Variegated.

*Type of variegation.*—One color and edged type of variegation with a central main vein of the same color as the edge-like the Anne variety.

*Width of colored edge.*—Medium — about 1.5 to 2. cm (0.6"-0.8") — like Veerle.

*Color of edge.*—Young and mature leaf near RHS Green 139A.

*Shading off of edge.*—Absent but with some diffuse bands inside the leaf blade — like Anne.

*Color of central part of blade.*—Young leaf RHS Yellow-Green 145C; mature leaf RHS Yellow-Green 145B.

Thus, the characteristics of the Morlem sport or mutation are substantially the same as the parental "Yellow Tropic" variety (the closest variety). More specifically, Morlem has the same growth habit and characteristics as the Amoena plants. Its capacity to form basal shoots and its vigor are comparable with Yellow Tropic parent plants. Its hardiness to temperature (optimum 18° to 25° C.) and diseases (particularly Erwinia bacterium) is comparable with the parent variety. In growing conditions in Antibes, France, shading in summer is preferable to avoid burns on leaves.

The main distinguishing characteristic of Morlem is the variegation of its foliage; the Morlem variety displays a light green yellow central macule covering more than 70% of the blade area and a regular defined dark green edge, that does not significantly invade the central macule with colored indentations as occurs with the other known members of the Amoena group. This gives to Morlem a significant element of distintiveness as compared with all previously known Dieffenbachia varieties. Furthermore, Morlem is neither less vigourous or slower growing nor smaller in height as compared with the Yellow Tropic parent plant because the quantity of active chlorophyll present in the lighter area of the leaf appears to be enough to enable the metabolism to reach the same performance as in the parent. Under normal growing conditions and depending on the type of color (i.e., 4 rotations/year in soil (or 3 rotations/year in containers), we obtain mature plants 70 cm high in 3 to 3½ months from 30-35 cm cane cuttings.

A certified copy of applicant's French De Demande De Certificat D'Obtention Vegetal No. 7791 June 13, 1988 is submitted concurrently herewith and is incorporated herein by reference.

We claim:

1. The new and distinct variety of Dieffenbachia cv. Morlem substantially as herein shown and described, said new variety being a sport of the Dieffenbachia cv. Yellow Tropic and being particularly characterized in its variegation that shows an extension of the yellow macule or coloration on the whoe leaf blade, excluding the central main vein and deliniated by a distinctive green colored edge that extends around the entire circumference of the leaf without significant indentations toward the middle of the limb, this pattern of variegation and the combination of the colored areas give the new variety a luminous look which is typical of the Morlem variety; otherwise the Morlem variety has the characteristics of the parental Yellow Tropic variety.

* * * * *